United States Patent [19]

Burres

[11] Patent Number: 5,397,352
[45] Date of Patent: Mar. 14, 1995

[54] METHOD OF RECOLLAGENATION

[76] Inventor: Steven Burres, 100 UCLA Medical Plz., Suite No. 522, Los Angeles, Calif. 90024

[21] Appl. No.: 113,211

[22] Filed: Aug. 27, 1993

[51] Int. Cl.$^6$ .............................................. A61F 2/02
[52] U.S. Cl. ...................................... 623/11; 623/15; 128/DIG. 8
[58] Field of Search ............. 623/11, 15; 128/DIG. 8, 128/898; 514/801; 604/274

[56] References Cited

U.S. PATENT DOCUMENTS

| | | | |
|---|---|---|---|
| 4,061,731 | 12/1977 | Gottlieb | 424/101 |
| 4,424,208 | 1/1984 | Wallace et al. | 424/177 |
| 4,427,808 | 1/1984 | Stol et al. | 524/24 |
| 4,516,276 | 5/1985 | Mittelmeier et al. | |
| 4,524,065 | 6/1985 | Pinnell | 424/94 |
| 4,582,640 | 4/1986 | Smestad et al. | 260/123 |
| 4,623,553 | 11/1986 | Ries et al. | 427/2 |
| 4,642,117 | 2/1987 | Nguyen et al. | 623/11 |
| 4,645,668 | 2/1987 | Pinnell | 424/94 |
| 4,780,450 | 10/1988 | Sauk et al. | 514/2 |
| 4,842,575 | 6/1989 | Hoffman, Jr. et al. | 600/36 |
| 4,877,805 | 10/1989 | Kligman | 514/381 |
| 5,137,875 | 8/1992 | Tsunenaga et al. | 514/21 |
| 5,295,980 | 3/1994 | Ersek | 604/272 |

FOREIGN PATENT DOCUMENTS

| | | | |
|---|---|---|---|
| 8906944 | 8/1989 | WIPO | 623/11 |
| 9217131 | 10/1992 | WIPO | 623/11 |

OTHER PUBLICATIONS

Arthur A. Beisang, III, M.D. et al., "Mammalian Response to Subderman Implantation of Textured Microimplants," *Aesthetic Plastic Surgery*, 16:83–90, 1992.

Edward C. Benzel, M.D., F.A.C.S. et al., "Histological Comparison of Autogenous Canine Fascia Lata, Gore–Tex, Lyophilized Human Fascia Lata, and Autogenous Canine Vein for Vascular Patch Graft Material in a Canine Arteriotomy Model," *Neurosurgery*, 31:1:108–113, Jul. 1992.

Charles N. Bertolami et al., "Preparation and Evaluation of a Nonproprietary Bilayer Skin Substitue," *Plastic and Reconstructive Surgery*, 1089–1098, Jun. 1991.

Jose L. Cisneros, M.D. et al., "Intradermal Augmentation with Expanded Polytetrafluoroethylene (Gore–Tex) for Facial Lines and Wrinkles," *J. Dermatol Surg. Oncol.*, 19:539–542, 1993.

S. K. Das et al., "The Fate of Free Autogenous Fascial Grafts in the Rabbit," *British Journal of Plastic Surgery*, 43:315–317, 1990.

Robert A. Ersek, M.D., "Bioplastique: A New Biphasic Polymer for Minimally Invasive Injection Implantation," *Aesthetic Plastic Surgery*, 16:59–65, 1992.

Algin B. Garrett, M.D. et al., "Carbon Dioxide Laser Treatment of Pitted Acne Scarring," *J. Dermatol Surg Oncol.* 16:8:737–740, 1990.

Mark J. Glasgold, M.D. et al., "The Use of Collagen Matrix to Enhance Closure of Facial Defects," *Ear, Nose and Throat Journal*, 70:8:531–537.

W. T. Green, Sr., "Fascia Grafts," *Transplantation Proceedings*, 8:2:1:113–118, Jun. 1976.

Ulrich T. Hinderer, M.D. et al., "Dermal and Subdermal Tissue Filling with Fetal Connective Tissue and Cartilage, Collagen, and Silicone: Experimental Study in the Pig Compared with Clinical Results. A New Technique of Dermis Mini–Autograft Injections," *Aesthetic Plastic Surgery*, 14:239–248, 1990.

Richard Hinton, M.D. et al., "A Biomechanical Analysis of Solvent–Dehydrated and Freeze–Dried Human (List continued on next page.)

Primary Examiner—Randall L. Green
Assistant Examiner—Rob Clarke
Attorney, Agent, or Firm—Lyon & Lyon

[57] ABSTRACT

A surgical method for implanting cadaver collagen for the restoration of lesions caused by the loss of collagen. The skin is perforated and a pocket is created under the skin. Human cadaver collagen is then introduced into the pocket and the skin perforation is closed. Over the next several months, the cadaver collagen is replaced by endogenous collagen.

8 Claims, 1 Drawing Sheet

OTHER PUBLICATIONS

Fascia Lata Allografts," *The American Journal of Sports Medicine*, 20:5:607–961, 1992.

Arnold Willaim Klein, M.D., Commentary: "Dermal Augmentation with Fat: A Reality?," *Soft Tissue Augmentation*.

Amos R. Koontz, M.D., "Experimental Results in the Use of Dead Fascia Grafts for Hernia Repair," *Annals of Surgery*, 83:523–536, 1926.

Gottfried Lemperle, M.D. et al., "PMMA Microspheres for Intradermal Implantation: Part I. Animal Research," *Annals of Plastic Surgery*, 26:1:57–63, Jan. 1991.

Ernest Aebi Major et al., "Studies on Autogenous and Homogenous Fascia Lata," *The Eye, Ear, Nose and Throat Monthly*, 50:18–26, Feb. 1971.

Sirpa E. Makisalo et al., "Collagen Types I and II and Fibronectin in Healing Anterior Cruciate Ligament After Reconstruction with Carbon Fibre," *Inquiry: the British Journal of Accident Surgery*, 20:72–76, 1989.

Angelo Mancuso et al., "The Abraded Punch Graft for Pitted Facial Scars," *J Dermatol Surg Oncol*, 17:2–34, 1991.

Larry Millikan, M.D. et al., "5-Year Safety and Efficacy Evaluation with Fibrel in the correction of Cutaneous Scars Following One or Two Treatments," *J Dermatol Surg Oncol*, 17:223–229, 1991.

Larry Millikan, M.D. et al., "Long-Term Safety and Efficacy with Fibrel in the Treatment of Cutaneous Scars—Results of a Multicenter Study,"*J. Dermatol Surg Oncol*, 15:8:837–842, Aug. 1989.

Richard A. Mladick, M.D., "Twelve Months of Experience with Bioplastique," *Aesthetic Plastic Surgery*, 16:69–76, 1992.

Frederick V. Nicolle et al., "Dermal and Facial Autografts in Facial Aesthetic Surgery," *Aesthetic Plastic Surgery*, 16:219–225, 1992.

Kevin S. Pinski, M.D. et al., "Autologous Fat Transplantation, Long-Term Follow-Up," *J. Dermatol Surg Oncol*, 18:179–184, 1992.

Jaime Planas, M.D. et al., "Twenty Years of Experience with Particulate Silicone in Plastic Surgery," *Aesthetic Plastic Surgery*, 16:53–57, 1992.

Sheldon V. Pollack, M.D., "Silicone, Fibre, and Collagen Implantation for Facial Lines and Wrinkles," *J. Dermatol Surg Oncol*, 16:10:957–960, Oct. 1990.

June K. Robinson, M.D. et al., "Injectable Collagen Implant: Histopathologic Identification and Longevity of Correction," *J. Dermaol. Surg. Oncol.*, 11:2:124–401, Feb. 1985.

Francois San-Galli, M.D. et al., "Experimental Evaluation of a Collagen-Coated Vicryl Mesh as a Dural Substitute," *Neurosurgery*, 30:3:396–401, Mar. 1992.

Rainer Schmelzle et al., "Results of Animal Experiments on the Transplantability of Cialit Preserved Human Fascia," *J. Max–Fac. Surg.*, 9:42–44, 1981.

Lee H. Silverstein, DDS, MS et al., "Bone Regeneration and Tissue Acceptace of Human Fascia Lata Grafts Adjacent to Dental Implants: A Preliminary Case Report," *Journal of Oral Implantology*, 18:4:394–398, 1992.

Hans-Henning Spitalny, M.D., "Corium Transplantation Cannula," *Aesthetic Plastic Surgery*, 17:157–161, 1993.

W. Stoll, M.D., "The Use of Polytetrafluoroethylene for Particular Augmentation of the Nasal Dorsum," *Aesthetic Plastic Surgery*, 15:233–236, 1991.

Krishna V. Thammavaram, M.D. et al., "Fascia Lata Graft as a Dural Substitute in Neurosurgery," *Southern Medical Journal*, 83:6:634–636, Jun. 1990.

M. Edward Wilson, M.D. et al., "Congenital Ptosis, Long-Term Results of Treatment Using Lyophilized Fascia Lata for Frontalis Suspensisons," *Ophthalmology*, 98:8:1234–1237, Aug. 1991.

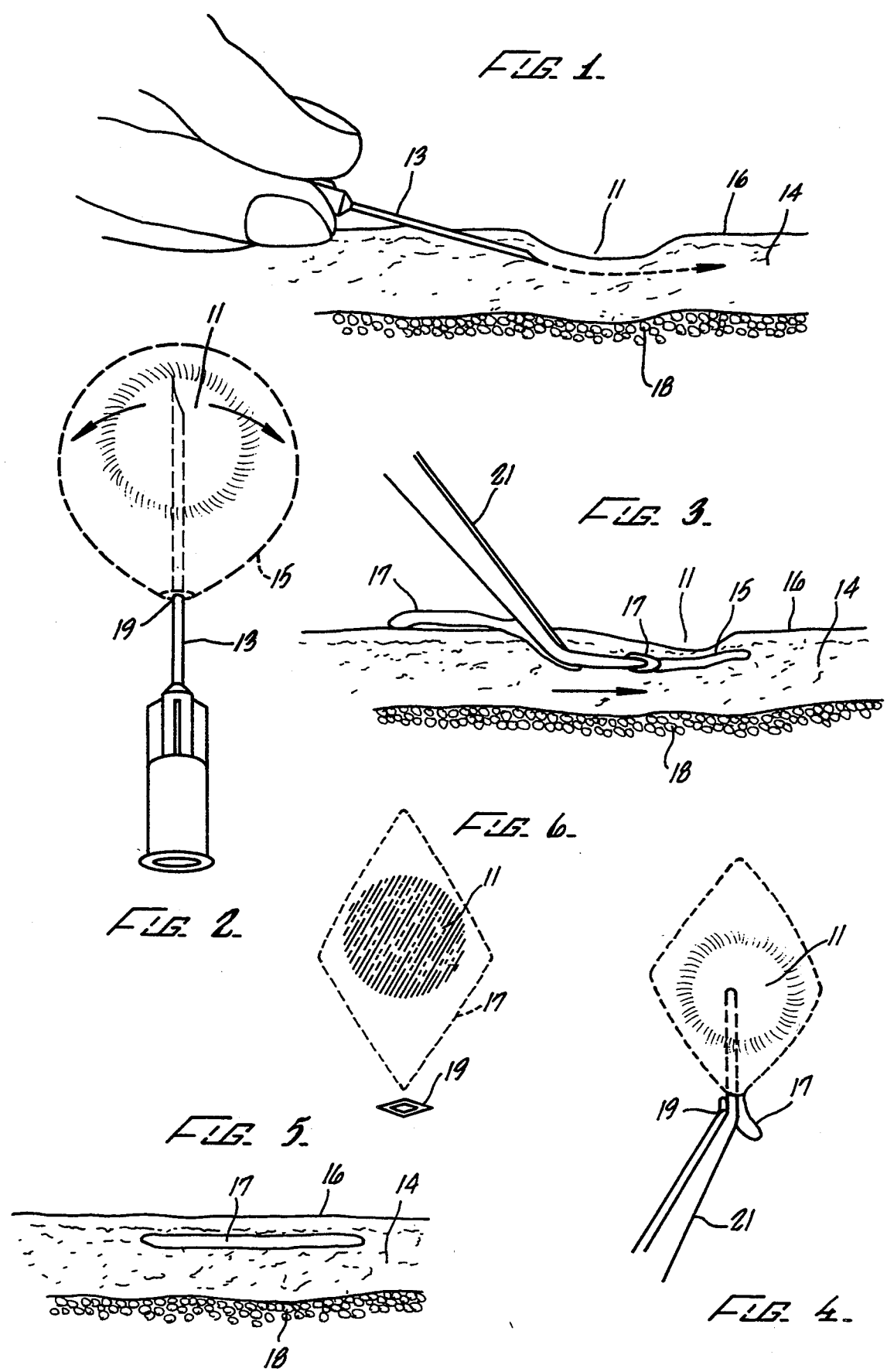

METHOD OF RECOLLAGENATION

BACKGROUND OF THE INVENTION

The field of the present invention is surgical methods for replacing and regenerating lost dermal collagen.

Disfiguring cutaneous irregularities, such as acne scars, wrinkles, and post traumatic depressions are a consequence of the loss of collagen that supplies the tissue thickness and maintains an even surface contour. Materials that have been used clinically to replace the lost tissue volume by subcutaneous injection include liquid silicone, fat, paraffin, liquid bovine collagen, and other fibrin compounds. Collagen suspensions, such as the liquid bovine collagen disclosed in U.S. Pat. Nos. 4,424,208, 4,582,640, and 4,642,117 are problematic in that they routinely fail to add endogenous collagen to tissue. Over time, the liquid disperses between cells allowing intercellular collagenase to digest the collagen substrate. Fat transferred from other areas is lumpy and has an unpredictable pattern of reabsorption. More resilient materials like silicone are gradually excreted into neighboring tissues from the depressed areas as the scar tightens again. Substances like paraffin can initiate an inflammatory response that causes further collagen loss. These filling techniques, in which liquid materials are injected through a needle into the scar, are disadvantageous because an injectable substance does not create a space between the layers of tissue in the recipient scar bed and therefore does not initiate new collagen deposition.

While laser treatments, dermabrasion and chemical peeling may stimulate the ingrowth of collagen from neighboring areas, they are seriously disadvantageous in that the nadir of the deepest scars and wrinkles cannot be safely treated, and hence the most noticeable defects remain unaffected. As a last resort when other techniques fail, the skin deformity may be completely excised and either sutured primarily or filled with punch grafts from neighboring areas. These techniques pose several risks including pigment changes, increased scarring, and persistent irregularities.

In fact, none of the above-described techniques affect the underlying problem which is the depletion of the collagen matrix that provides a natural support for epidermal growth. Unless fresh collagen is generated within the depression, the restored topography has dubious longevity.

SUMMARY OF THE INVENTION

The present invention, entitled "Recollagenation," is directed to the application of implantable cadaver material for the restoration of lesions caused by the loss of collagen. After delineating, anesthetizing, and sterilizing the site to be treated, the skin is perforated and a pocket is created. Human cadaver collagen is then introduced through the skin perforation and placed into the pocket. Then the skin perforation is closed. Over the next several months, the cadaver collagen is replaced by endogenous collagen. This endogenous collagen may reorganize and change shape but provides permanent restoration.

Accordingly, it is an object of the present invention to provide a surgical method to restore lesions with human cadaver collagen. Other and further objects and advantages will appear hereinafter.

BRIEF DESCRIPTION OF THE DRAWINGS

FIG. 1 is a sectional view of a skin depression illustrating the needle puncture of the skin adjacent to the depression.

FIG. 2 is a plan view illustrating the creation of an intradermal pocket by swiveling the needle.

FIG. 3 is a sectional view illustrating the introduction of cadaver collagen into the intradermal pocket.

FIG. 4 is a plan view of FIG. 3.

FIG. 5 is a section view of the skin with the cadaver collagen in the intradermal pocket.

FIG. 6 is a plan view of FIG. 5.

DETAILED DESCRIPTION OF THE PREFERRED EMBODIMENTS

Patients with depression anywhere in their skin surface are candidates for this procedure. The skin depression can be the result of many natural or pathological causes including acne, chicken pox, trauma, age, irregular fat deposits (cellulite), and infections, to name a few. The patients are medically screened to determine if they are suitable for recollagenation therapy. Areas of active infection, healing, or inflammation are typically excluded from treatment. Patients may not be candidates for treatment if they suffer from any underlying skin or collagen disorders, such as scleroderma.

Initially, the site to be treated is delineated with a surgical ink marker and anesthetized by a 1% lidocaine solution with 1:100,000 epinephrine. Then, the site is sterilized with an iodine preparation.

Turning in detail to the drawings, FIGS. 1 and 2 illustrate a skin depression 11. The skin adjacent to the skin depression 11 is punctured with a needle 13, preferably a 20 gauge needle. An intradermal pocket 15 is created by swiveling the needle 13 through the dermis 14 without reperforating the epidermis 16 but still maintaining the dissection plane as superficial as possible staying above the subcutaneous fatty tissue layer 18. The needle undermining is broadened until the pocket 15 is slightly wider than the cutaneous defect 11 and all adhesive tissue bands within the pocket 15 are divided by the needle's blade.

FIGS. 3 and 4 illustrate the insertion of a cadaver human collagen graft 17 into the intradermal pocket 15. Freeze-dried cadaver human collagen is cut into thin strips or small chips to fit the appropriate recipient pocket 15. Then the collagen is soaked in a supersaturated solution of sugar, typically glucose, which functions as a tissue syrup to facilitate the introduction of the material through the needle perforation 19. Using a curved delicate forceps 21, the graft 17 is then slid into the pocket through the needle hole 19.

FIGS. 5 and 6 illustrate the graft 17 within the dermis 14 and above the subcutaneous fatty tissue layer 18. Finally, the needle hole 19 may be sealed by either the use of flexible collodion or sewn closed with a single stitch of 6-0 nylon as required. After one week the collodion may be peeled away or the suture may be removed.

Pathologic studies demonstrate that implanted human cadaver collagen based tissue such as fascia lata, dura, or tendon is replaced by endogenous collagen over a two to six month period, eliminating any residual products of the original implant. R. Schmetzle et al., "Results of Animal Experiments on the Transplantability of Cialit ® Preserved Human Fascia," *J. Max-Fac. Surg.*, 42:9 (1981) and K. Das et al., "The Fate of Free Autogenous Fascial Grafts in the Rabbit," *British J. of Plastic Surgery*, 43:315–317 (1990). Because the implant is solid it functions as a cast that displaces the body's own tissues, resulting in a scar reaction that generates native collagen to rebind the area.

A good source of human cadaver collagen is banked fascia lata from the American Red Cross. This particular material has been harvested by the donor, trimmed, and freeze-dried over a seventy-two hour period and shipped out in vacuum. Banked material is preferred to fresh material because it has a known density and hydration that gives a predictable collagen response. Other types of tissue processing may be satisfactory also. Additionally, other sources of human cadaver collagen, such as dura or tendon, can be used.

The following examples are presented for the purpose of illustrating the invention.

EXAMPLE #1

A patient with a history of chronic acne is medically screened and found qualified for recollagenation therapy. The patient then receives numerous recollagenation grafts to the forehead and cheek regions in the area of previously depressed acne scars without active inflammation. At five week follow-up, several of these scars may be retreated to achieve maximum elevation. Therapy is thereafter terminated when all depressed scars are sufficiently elevated.

EXAMPLE #2

A patient with a disfiguring depressed scar resulting from an earlier trauma is medically screened and found suitable for recollagenation therapy. The scar of approximately five centimeters in length and one centimeter wide is elevated in various areas. Recollagenation grafts ranging in length from five millimeters to fifteen millimeters may be inserted. Further sessions may be required to completely elevate the scar to its maximum height, at which point therapy is terminated.

EXAMPLE #3

An elderly patient with multiple facial wrinkles of the forehead, eyelids, mouth, and naso-labial regions is medically screened and found suitable for recollagenation therapy. Numerous strips of banked fascia lata are used to fill the wrinkle lines on both sides of the face. At a five week follow-up visit, several more recollagenation grafts may need to be inserted. Therapy is terminated when all the wrinkles are adequately elevated.

EXAMPLE #4

A patient with multiple chicken pox scars in the forehead, nose and chin regions is medically screened and found suitable for recollagenation therapy. Scars may be treated with custom sized grafts in a single session.

In view of the preceding description, further modifications and alternative embodiments of the invention will be apparent to those skilled in the art. Accordingly, the preceding descriptions and examples are to be construed as explanatory and illustrative only for the purpose of teaching and enabling those skilled in the art to practice this invention. It should be understood that cadaver human fascia lata is the preferred material because of its configuration and that other forms of banked collagen may produce similar results. Any region of the body in which collagen has been lost can be restored in this fashion. In a similar manner, collagen enhancement may be performed on normal structures, e.g., lips, as desired.

While the preferred embodiment of the above-described invention is to be understood as the best mode presently contemplated it is, by no means, the only embodiment possible. The scope of the invention is defined by the following claims and by any equivalent modifications and variations that fall within the true spirit of the invention.

What is claimed:

1. A method of recollagenation comprising:
   a. identifying a skin depression for elevation;
   b. perforating the skin with a needle adjacent to the said skin depression;
   c. creating a pocket underneath the skin surface over said skin depression by swiveling said needle through the dermis;
   d. cutting at least one strip or chip of freeze dried banked human fascia lata to be placed in said pocket;
   e. soaking said strip or chip of fascia lata in a supersaturated sugar solution;
   f. inserting said strip or chip of fascia lata through said skin surface above said pocket; and
   g. closing said skin perforation.

2. The method of claim 1 wherein said skin depression is a scar.

3. The method of claim 2 wherein said scar is an acne scar.

4. The method of claim 2 wherein said scar is a chicken pox scar.

5. The method of claim 1 wherein said skin depression is a wrinkle.

6. The method of claim 1 wherein said skin depression is a fatty depression commonly referred to as cellulite.

7. The method of claim 1 wherein said strip or chip of banked human fascia lata is cut to the same size of said pocket.

8. The method of claim 1 wherein said supersaturated sugar solution is a supersaturated glucose solution.

* * * * *